(12) United States Patent
Wood

(10) Patent No.: US 6,365,115 B1
(45) Date of Patent: Apr. 2, 2002

(54) STERILIZATION AND STORAGE CONTAINER TRAY

(75) Inventor: Timothy E. Wood, Weare, NH (US)

(73) Assignee: Poly Vac, Inc., Manchester, NH (US)

( * ) Notice: Subject to any disclaimer, the term of this patent is extended or adjusted under 35 U.S.C. 154(b) by 0 days.

(21) Appl. No.: 09/312,127

(22) Filed: May 14, 1999

(51) Int. Cl.[7] .............................. A61L 2/00; B65D 6/28; B65D 8/10; A61B 17/06

(52) U.S. Cl. ...................... 422/292; 422/300; 220/4.01; 220/611; 220/612; 220/613; 220/622; 206/370; 206/438

(58) Field of Search ............................. 422/28, 292, 300; 220/611, 4.01, 612, 613, 622; 206/370, 438

(56) References Cited

U.S. PATENT DOCUMENTS

| | | | | |
|---|---|---|---|---|
| 1,887,761 A | * | 11/1932 | Hauser | |
| 4,188,037 A | * | 2/1980 | Abbes et al. | 277/2 |
| 4,493,860 A | * | 1/1985 | Callahan | 427/230 |
| 4,627,542 A | | 12/1986 | Fredrickson | 211/150 |
| 4,643,303 A | | 2/1987 | Arp et al. | 206/370 |
| 4,725,507 A | * | 2/1988 | Lescaut | 428/551 |
| 4,728,504 A | | 3/1988 | Nichols | 422/297 |
| 4,753,368 A | * | 6/1988 | Lescaut | 220/454 |
| 4,783,321 A | | 11/1988 | Spence | 422/300 |
| 5,004,116 A | * | 4/1991 | Cattaorzzi | 220/4.34 |
| 5,248,030 A | * | 9/1993 | Tarozzi | 206/1.7 |
| 5,279,800 A | | 1/1994 | Berry, Jr. | 422/300 |
| 5,281,400 A | | 1/1994 | Berry, Jr. | 422/295 |
| 5,384,103 A | | 1/1995 | Miller | 422/310 |
| 5,441,707 A | | 8/1995 | Lewis et al. | 422/300 |
| 5,441,709 A | * | 8/1995 | Berry, Jr. | 422/297 |
| 5,490,975 A | * | 2/1996 | Dane | 422/300 |
| 5,816,403 A | * | 10/1998 | Wilkes et al. | 206/438 |
| 5,882,612 A | * | 3/1999 | Riley | 422/300 |

FOREIGN PATENT DOCUMENTS

DE    295 03 691 U1    8/1995    .......... B65B/55/24

* cited by examiner

Primary Examiner—Robert J. Warden, Sr.
Assistant Examiner—Monzer R. Chorbaji
(74) Attorney, Agent, or Firm—Taylor & Aust, P.C.

(57) ABSTRACT

A surgical tray comprises a frame made of a synthetic plastic material having a metal plate insert floatably mounted in the frame and forming the tray bottom or floor.

12 Claims, 4 Drawing Sheets

STERILIZATION AND STORAGE CONTAINER TRAY

FIELD OF THE INVENTION

This invention relates to sterile container systems generally, and more particularly to container systems for the sterilization and subsequent sterile storage of medical surgical instruments and the like.

BACKGROUND OF THE INVENTION

Surgical procedures are regularly performed using "sets" of pre-selected surgical instruments, each set being a collection of instruments established from experience to be useful in a given surgical procedure. For example, the surgical instruments expected to be used in an obstetrical procedure are grouped together to form a set and, as a set, are sterilized, stored in a pan or tray, and finally transported on that tray to the operating room when their use is required.

Sterilization of reusable and delicate, precision surgical instruments and their subsequent sterile storage is of paramount concern to surgeons and hospitals. Sterilized surgical instruments are essential during surgical procedures to minimize the risk of infection.

Some example prior art patents which provide for sterilization containers are Arp et al, U.S. Pat. No. 4,643,303; Nichols, U.S. Pat. No. 4,728,504 and Spence, U.S. Pat. No. 4,783,321. These prior art patents generally teach the use of baskets or trays to hold the instruments to be sterilized, and apertures in the baskets which allow for gross drainage of condensation from the baskets first to the container floor below the basket, and from the container floor to the outside.

U.S. Pat. No. 4,643,303 describes a sterilization container enclosing an instrument basket within a box-like base and cover. The container also includes clamps mounted to the container by hinges for releasably holding the cover to the base. U.S. Pat. No. 4,783,321 describes a sterilization container enclosing an instrument basket within a base and cover. The container also includes a latch mechanism for releasably holding the cover to the base.

Most of the prior art, for example, Nichols U.S. Pat. No. 4,728,504, provide for the placement of the instruments on a removable basket or tray which includes apertures formed on the bottom of the tray to allow for the drainage of condensation. The domed configuration of the tray bottom in U.S. Pat. No. 4,728,504 reportedly allows for sufficient surface area contact with the instruments such that condensate may be held between the instruments and the tray after sterilization. Such a risk of airborne bacterial contamination of remaining condensation after sterilization increases during increased storage of the sterilized instruments. Thus, it is imperative to remove as much condensation as possible from the container and from the instruments after sterilization.

Originally, sterilization trays were made of metal. Metal had an advantage in that it has a relatively high thermal mass, thus leading to improved evaporation of steam or other sterilant following exposure to the steam or sterilant. However, metal is difficult to work with and is heavy. Also, metal could dull or nick delicate surgical instruments. Accordingly, more recently, advances in high temperature resistant plastics have led to the commercialization of sterilization trays made of plastic. Plastic has certain advantages over metal. For one, the trays may be molded. Also, trays made of plastic weigh significantly less than trays made of metal. On the other hand, plastic has a significantly lower thermal mass than metal. Thus, trays made of plastic are not as forgiving as metal trays.

SUMMARY OF THE INVENTION

The present invention provides an improved sterilization, transporting and storage container tray for surgical instruments. More particularly, according to the present invention, a surgical tray is provided comprising a frame made of a synthetic plastic material, and having a metal plate insert mounted in the frame and forming the tray bottom or floor. In order to accommodate different rates of thermal expansion, the metal plate insert is attached to the plastic frame by means of resiliently deformable or floating fasteners. Alternatively, the metal insert plate is floated in the frame.

BRIEF DESCRIPTION OF THE DRAWINGS

Further objects and advantages of the present invention will be seen from the following detailed description, taken in conjunction with the accompanying drawings, wherein like numerals depict like parts, and wherein.

DETAILED DESCRIPTION OF PREFERRED EMBODIMENT

Figure 1:
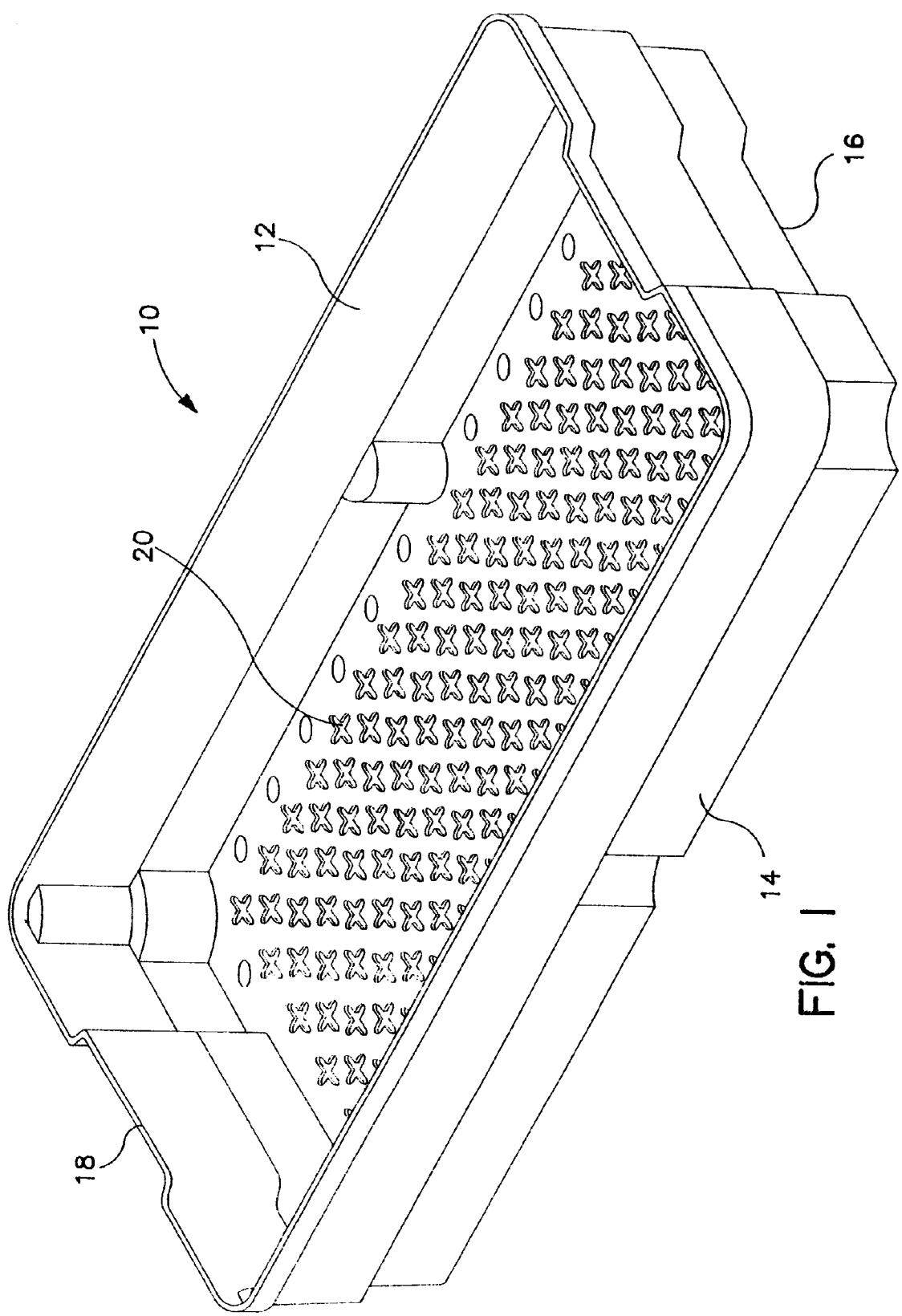
FIG. 1 is a side perspective View of a sterilization tray made in accordance with the present invention.
Figure 2:
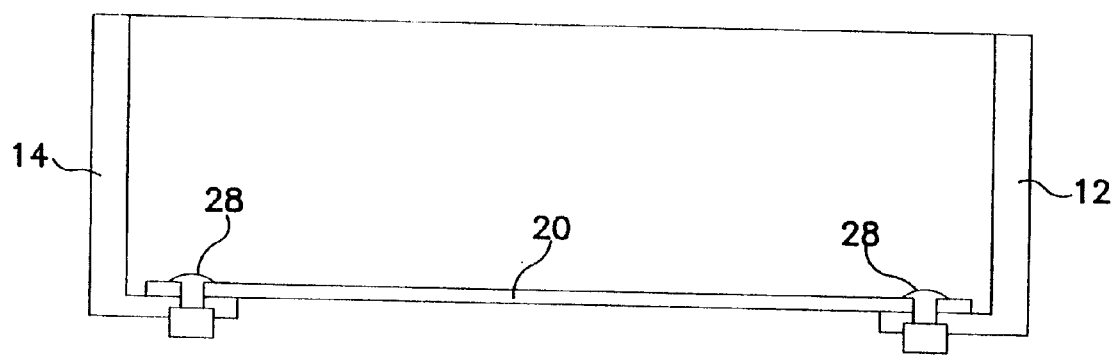
FIG. 2 is a cross-sectional view taken along lines II—II of FIG. 1.

Referring to FIGS. 1–4 the drawings, the sterilization tray in accordance with the present invention comprises a pair of side walls 12, 14 and a pair of end walls 16, 18 defining a generally rectangular open frame 10. Side and end walls 12, 14, 16 and 18 comprise generally L-shaped members in cross section, and preferably are formed as a continuous frame element, e.g. by molding, However, the side and end walls may comprise extruded members joined together at the corners, for example, by mechanical fastening means or snap fittings, or by means of an adhesive or by means of plastic welding.

Mounted within the frame 10 and forming a base wall thereof is a metal plate 20. Metal plate 20 is formed of a rust-resistant material such as aluminum or stainless steel plate. A plurality of ventilation/mounting holes 22 are formed through plate 20, e.g. by stamping or drilling. Preferably holes 22 comprise cruciform shaped holes in accordance with the teachings of copending application Ser. No. 09/312,126, filed May 14, 1999 and assigned to the common assignee.

Figure 3:
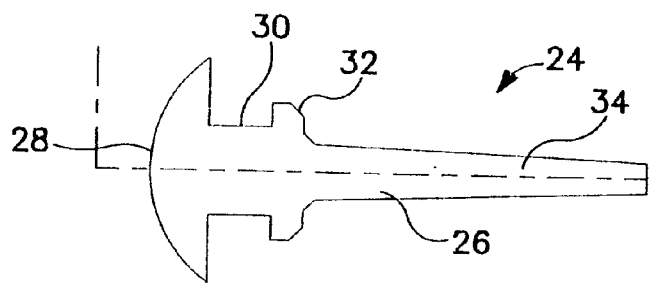
FIG. 3 is a side elevation view of a rivet useful in accordance with the present invention.
Figure 4:
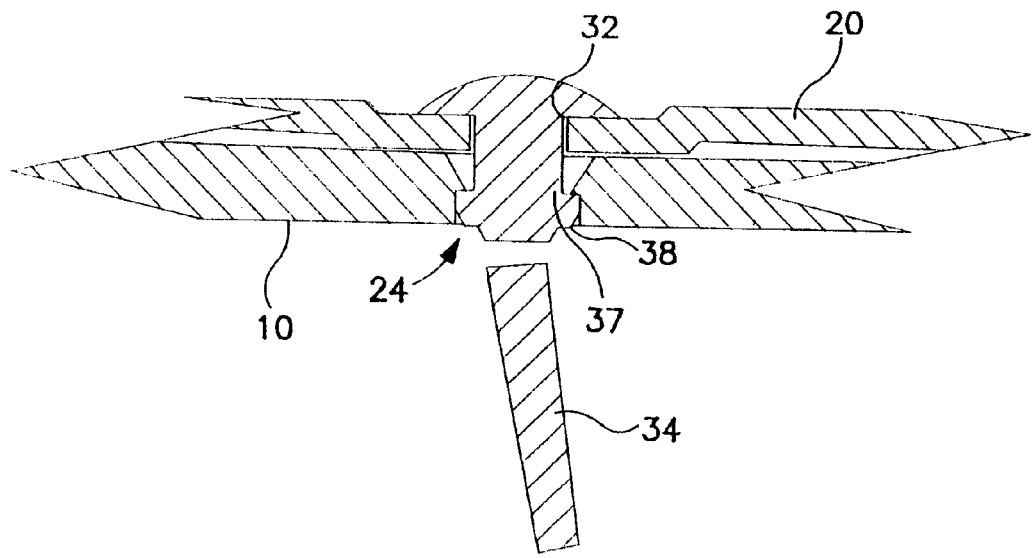
FIG. 4 is an enlarged view of the indicated portion of FIG. 2.

Referring in particular to FIGS. 3 and 4, plate 20 is mounted in frame 10 by means of resilient mounting members which in a preferred embodiment comprises silicone rubber rivets 24, Silicon rubber rivets 24 each comprise an elongate body 26 including a flanged head 28, a reduced neck portion 30 and a retaining ring 32, and an elongated tail 34 which extends from retainer ring 32. Plate 20 is mounted in frame 10 by means of rivets 26 which extend through holes 32 formed in the peripheral edges of plate 20 in alignment with matching holes 36 formed in the frame 10. As can be seen in particular in FIG. 4, hole 32 is slightly oversized as compared to neck 30, while hole 36 includes step portion 37 and 38 which are sized so as to snugly capture the neck 30 and retaining ring portions 30 of rivets 24.

Assembly of plate 20 to frame 10 is quite straightforward. The plate is located in the frame with holes 32 aligned with holes 36. Then, rivets 24 are pressed and pulled through holes 32 and 36. Finally, tail portions 34 are cut off leaving rivets 24 more or less flush with the bottom of the tray.

Figure 5:
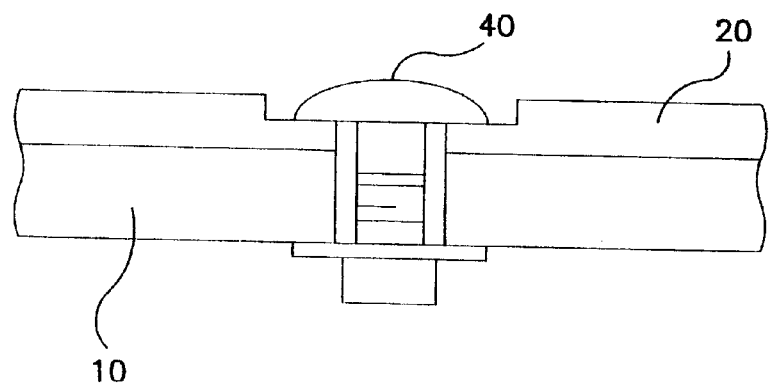
FIGS. 5 to 7 show alternative embodiments of the invention.

Rivets 24 are formed of resiliently deformable material compatible with sterilization conditions such as medical grade silicone rubber. Forming rivets 26 of medical grade silicone rubber has the advantage in that the silicone rubber is highly resiliently deformable and thus accommodates for differences in the coefficients of thermal expansion of metal plate 20 and plastic frame 10. It should be noted, however, that other means may be employed for mounting metal plate 20 in plastic frame 10. For example, as seen in FIG. 5, metal plate 20 may be mounted to frame 10 using other types of fasteners including, for example, interference fit fasteners, threaded fasteners, clips, etc., made of plastic, nylon or metal. For example, in the case of screw fasteners or the like, the fasteners 40 may have oversized heads and/or washers. It should be noted that where metal fasteners are used, the holes through the metal plate 20 and the plastic frame 10 should be made sufficiently oversized to accommodate anticipated differences in thermal expansion between the metal plate 20 and plastic frame 10.

Figure 6:
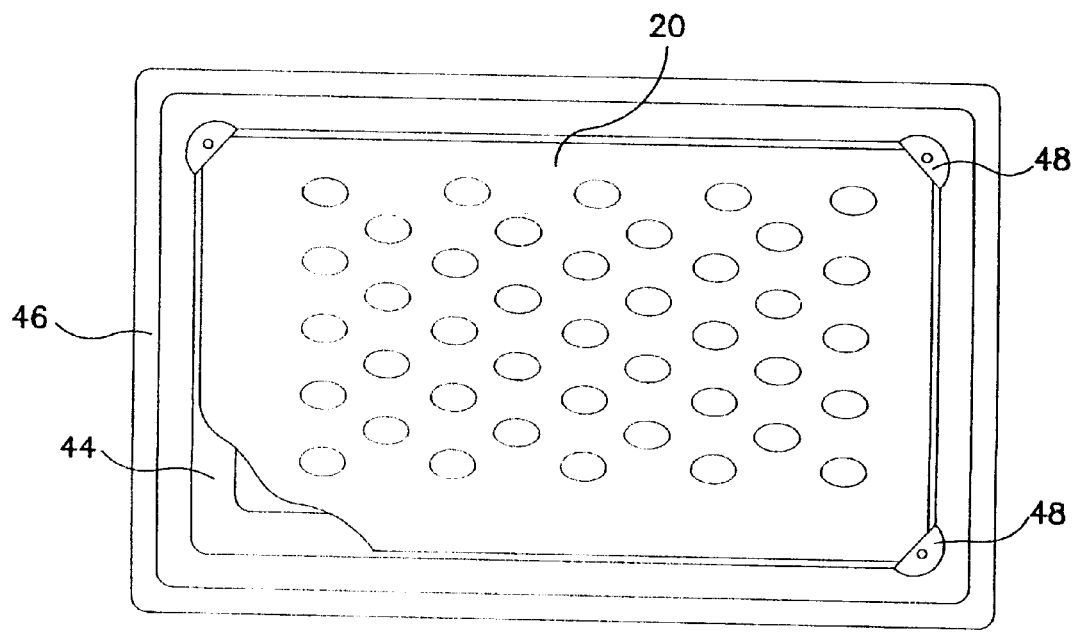
Figure 7:
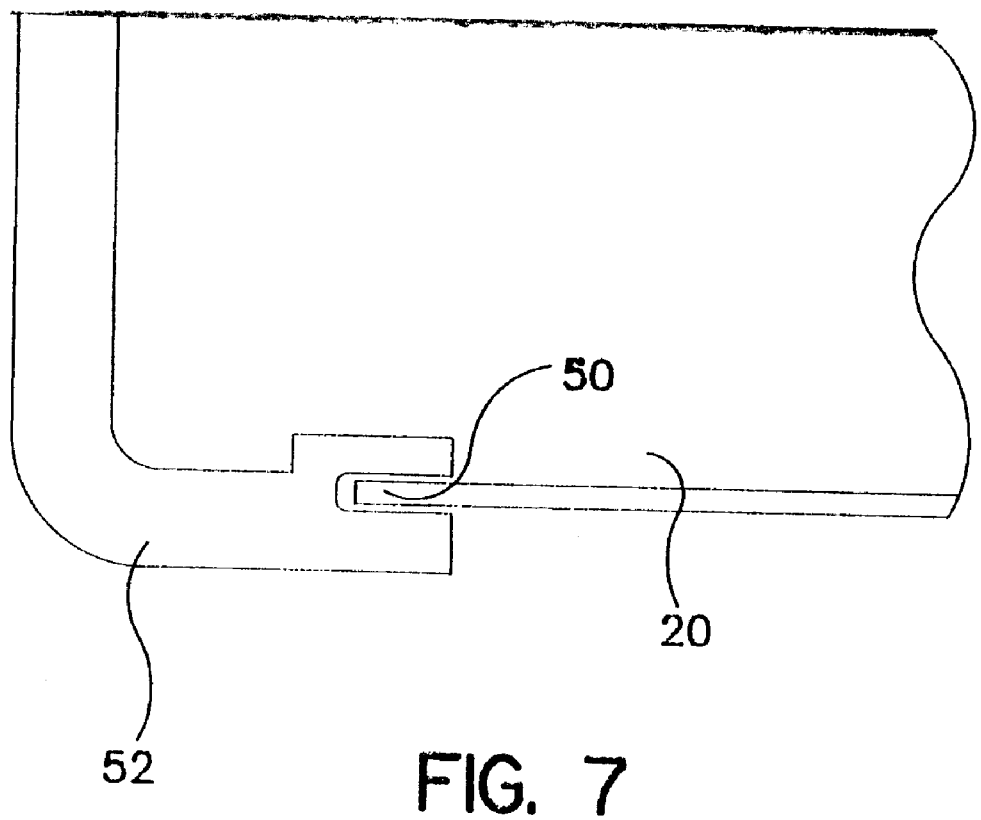

FIG. 6 illustrates yet another embodiment. In the FIG. 6 embodiment metal plate 20 is located in an L-shaped peripheral groove 44 formed in plastic frame 46, and is held in the plastic frame by corner brackets 48 which permit the metal plate to float in the frame, Referring to FIG. 7, in yet another embodiment, the metal plate 20 is captured in a channel 50 formed in the frame 52. In order to facilitate assembly, frame 52 may be formed in two or more pieces and joined together by means of suitable fasteners, snap fittings or adhesive.

Yet other changes made be made without departing from the spirit and scope of the invention.

What is claimed is:

1. A sterilization tray assembly comprising a rectangularly shaped plastic frame including plastic sidewalls and plastic end walls, said plastic frame having floatably mounted therein a metal plate which forms a bottom of the tray, said metal plate having ventilation and mounting holes/apertures formed therein.

2. The sterilization tray of claim 1, wherein said metal plate is formed of aluminum.

3. The sterilization tray of claim 1, wherein said metal plate comprises stainless steel.

4. The sterilization of claim 3, wherein said plastic frame is formed of at least two pieces which are joined together by means of snap fittings.

5. The sterilization tray of claim 3, wherein said plastic frame is formed of at least two pieces which are joined together by means of an adhesive.

6. The sterilization tray of claim 1, wherein said metal plate is affixed to the frame by means of resiliently deformable fasteners.

7. The sterilization of claim 6, wherein said resiliently deformable fasteners comprise rivets formed of a resiliently deformable material.

8. The sterilization tray of claim 6, wherein said resiliently deformable fasteners are formed of silicone rubber.

9. The sterilization tray of claim 1, wherein said metal plate is floatably mounted to said plastic frame by means of fasteners extending through oversized holes.

10. The sterilization tray of claim 1, wherein said a metal plate is floatably mounted in a groove in said frame and is held in said plastic frame by brackets.

11. The sterilization tray of claim 1, wherein said metal plate is supported in a channel formed in said plastic frame.

12. The sterilization tray of claim 11, wherein said plastic frame is formed of at least two pieces which are joined together by means of a fastener.

* * * * *

UNITED STATES PATENT AND TRADEMARK OFFICE
CERTIFICATE OF CORRECTION

PATENT NO.      : 6,365,115 B1
DATED           : April 2, 2002
INVENTOR(S)   : Timothy E. Wood It is certified that error appears in the above-identified patent and that said Letters Patent is hereby corrected as shown below:

Column 2,
Line 24, delete "View" and substitute -- view -- therefor.

Column 3,
Line 33, after "frame" delete "," and substitute -- . -- therefor.

Signed and Sealed this

Nineteenth Day of August, 2003

JAMES E. ROGAN
*Director of the United States Patent and Trademark Office*